(12) United States Patent
Herman

(10) Patent No.: US 8,435,248 B2
(45) Date of Patent: May 7, 2013

(54) PROBE TIP AND INFUSION SLEEVE FOR USE WITH OPHTHALMOLOGICAL SURGERY

(75) Inventor: Wesley K. Herman, Dallas, TX (US)

(73) Assignee: Wesley K. Herman, Dallas, TX (US)

( * ) Notice: Subject to any disclaimer, the term of this patent is extended or adjusted under 35 U.S.C. 154(b) by 801 days.

(21) Appl. No.: 12/169,483

(22) Filed: Jul. 8, 2008

(65) Prior Publication Data

US 2009/0093750 A1    Apr. 9, 2009

Related U.S. Application Data

(60) Provisional application No. 60/977,705, filed on Oct. 5, 2007.

(51) Int. Cl.
*A61F 9/00* (2006.01)
(52) U.S. Cl.
USPC .......................................... 606/107

(58) Field of Classification Search .......... 600/459, 600/471; 604/22, 35, 44, 46, 48, 118–119, 604/264, 268, 272, 902; 606/107, 169
See application file for complete search history.

(56) References Cited

U.S. PATENT DOCUMENTS

| | | | |
|---|---|---|---|
| 5,725,495 A * | 3/1998 | Strukel et al. | 604/44 |
| 5,814,010 A | 9/1998 | Ziegler | |
| 5,919,157 A | 7/1999 | Strukel | |
| 5,993,409 A | 11/1999 | Maaskamp | |
| 6,299,591 B1 | 10/2001 | Banko | |
| 7,204,820 B2 | 4/2007 | Akahoshi | |
| 2004/0199192 A1 * | 10/2004 | Akahoshi | 606/169 |
| 2006/0264970 A1 | 11/2006 | Ernest et al. | |

* cited by examiner

*Primary Examiner* — Ryan Severson
*Assistant Examiner* — Ashley Cronin
(74) *Attorney, Agent, or Firm* — Howison & Arnott, L.L.P.

(57) ABSTRACT

A phacoemulsification probe includes a first portion for interconnecting the probe with a phacoemulsification machine. A probe tip has a first end connected with the first portion and a second end curved up to a predetermined angle. The probe tip defines a channel therein for aspirating material through the probe tip from a surgical region.

15 Claims, 7 Drawing Sheets

PROBE TIP AND INFUSION SLEEVE FOR USE WITH OPHTHALMOLOGICAL SURGERY

CROSS-REFERENCE TO RELATED APPLICATIONS

This application claims priority from U.S. Provisional Application No. 60/977,705, entitled "PROBE TIP AND INFUSION SLEEVE FOR PHACO EMULSIFICATION PROCESS FOR REMOVING THE HUMAN LENS IN CATARACT SURGERY AND REFRACTIVE LENS PROCEDURES," filed Oct. 5, 2007, which is incorporated herein by reference.

TECHNICAL FIELD

The present invention relates to probe tips for use in the removal of a human lens from an individual's eye, and more particularly, to a curved probe tip and sleeve design for use with optical procedures such as cataract surgery and refractive and presbyopic lens exchange surgery.

BACKGROUND

Phacoemulsification techniques for the removal of cataracts or the removal of a human lens in an individual's eye for purpose of refractive lens correction requires the use of high frequency ultrasound generated movements of a metal probe tip combined with the infusion of fluids to maintain and pressurize the human eye. The device for providing these functionalities is generally referred to as a phacoemulsification probe. The phacoemulsification probe uses subtle aspiration or suction functions to remove emulsified lens material within the eye of an individual. The material within the eye may be emulsified using ultrasonic processes in order to break down material within the eye. These types of probes are used during cataract surgery, as well as for lens removal purposes for refractive and presbyopic lens correction. In currently used technologies, the phacoemulsification probes, their tips and associated sleeves, are designed to generate linear movement of the tip via ultrasound and to provide the coaxial infusion of fluids within the eye by a sleeve which projects fluid in the same direction as tip movement. However, this infusion of fluid is in a competitive direction to the direction of suction of the probe tip which is used for aspirating lens material that has been emulsified via the ultrasonic emissions of the probe tip.

The configuration of existing phacoemulsification probes use straight probe tips having the infusion sleeve coaxial with the probe tip to inject fluid along the same axis as the ultrasonic emissions of the probe tip. This generates a more linear to and fro motion with respect to the straight or beveled tip of the phacoemulsification probe that can potentially run the risk of damaging sensitive support structures of the human lens, such as zonules. The linear back and forth movement of existing probes can cause damages to the inner structures of the capsular sac or support structures of the lens since the movements may be directly into the structures and the fluidic infusion may also be directly at the structures in addition to the ultrasonic emissions of the tip. These combined forces can, for example, cause turbulent endotheliopathy, which may damage the inside of the lining of the cornea.

Another problem arising from the linear to and fro motion of existing phacoemulsification probes, arises from "coring." "Coring" involves a situation wherein the tip of the phacoemulsification probe becomes plugged with emulsified materials that are being broken down and aspirated, particularly during linear emulsification techniques. Thus, there is a need for an improved phacoemulsification tip for use in ophthalmological procedures involving the removal of materials from the capsular lens sac that overcomes the problem of existing tips such as projection of fluids in a non competitive direction from which materials are attempting to be aspirated, risking damage to sensitive and internal structures of the human eye, and the prevention of coring when using phacoemulsification probes.

SUMMARY

The present invention as disclosed and described herein, in one aspect thereof, comprises a first portion for interconnecting the probe tip with a probe body. A probe tip has a first end connected with the first portion and a second end curved to a predetermined angle. The probe tip defines a channel therethrough for aspirating material from a surgical region through the probe tip.

BRIEF DESCRIPTION OF THE DRAWINGS

For a more complete understanding, reference is now made to the following description taken in conjunction with the accompanying Drawings in which.

DETAILED DESCRIPTION

Figure 1:
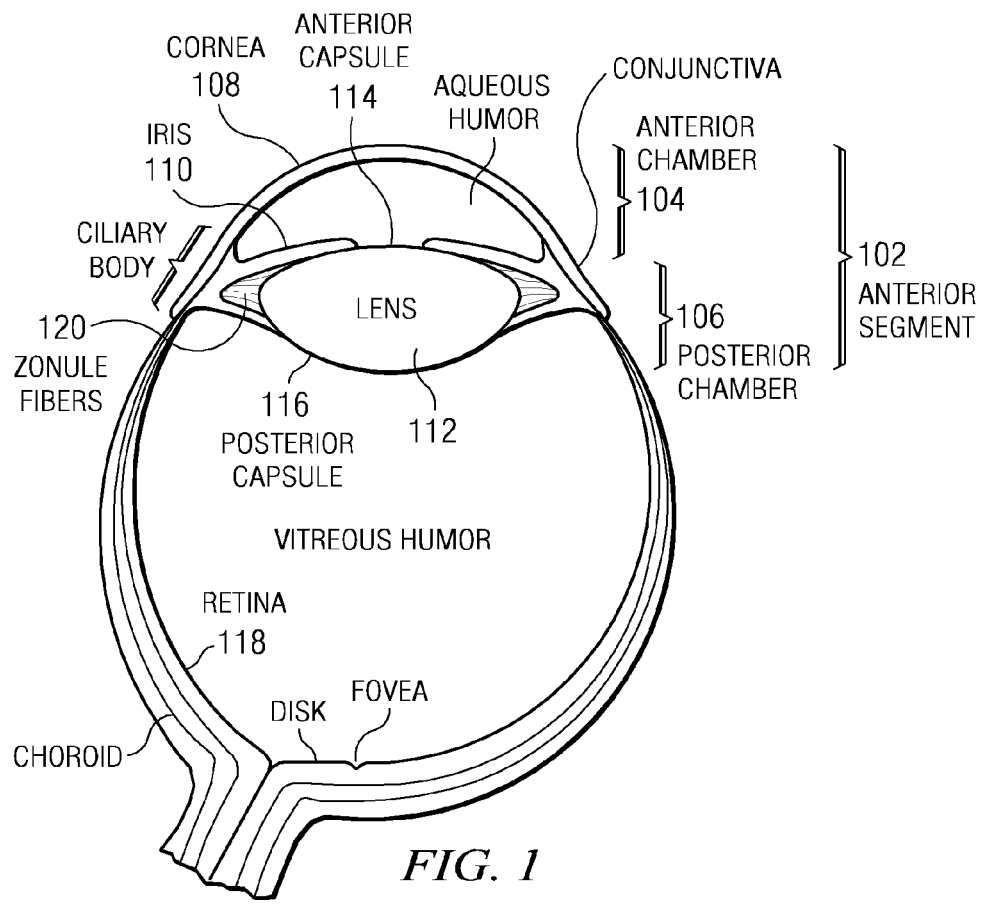
FIG. 1 illustrates the various structures of a human eye.

Referring now to the drawings, wherein like reference numbers are used herein to designate like elements throughout, the various views and embodiments of the probe tip and infusion sleeve for use with ophthalmological surgery are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Referring now to the drawings, and more particularly to FIG. 1, there is provided an illustration of the major structures of the human eye. The structures involved with the phacoemulsification and other optical procedures relevant to the improved phacoemulsification probe tip and sleeve of the present disclosure are all within the anterior segment 102 consisting of the anterior chamber 104 and the posterior chamber 106. The anterior chamber 104 comprises those structures from the cornea 108 to the iris 110. The cornea 108 covers the anterior chamber 104 and comprises the exterior of the eye. The iris 110 expands and retracts to alter the size of the pupil and adjust the amount of light entering the human eye. The lens 112 is used for focusing light passing through the pupil on the retina 118. The lens 112 is contained within the capsular sac consisting of the anterior capsule 114 and the posterior capsule 116. Zonule fibers 120 are used for supporting the lens 112 within the capsular sac. A cataract is an opacity that develops within the lens 112. Cataract surgery or refractive lens procedures involve a process for piercing the anterior capsule 114 to remove the lens 112 and other materials contained within the capsular sac.

Figure 2:
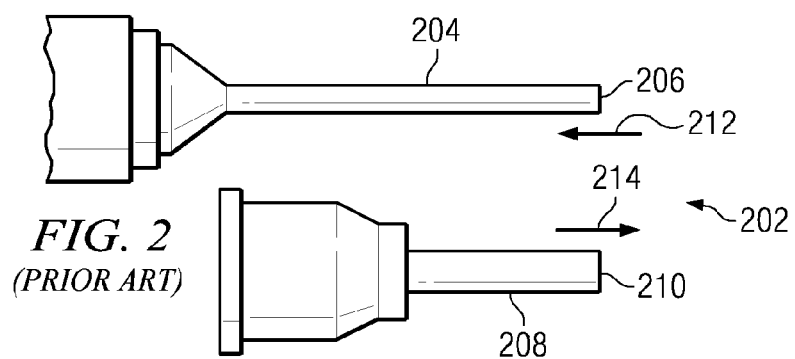
FIG. 2 illustrates a prior art phacoemulsification tip and associated sleeve.

Referring now to FIG. 2, there is illustrated a prior art phacoemulsification probe that is used for removing cataract and lens material from the capsular sac of a human eye. The phacoemulsification probe 202 consists of a stainless steel or metal tip 204 that is inserted within an incision made within the cornea and anterior capsule to aspirate emulsified material through a small opening 206 within the end of the probe tip 204. Additionally, a fluidic sleeve 208 is placed over the probe tip 204 and a fluid material may then be injected along the axis of the tip 205 through the annular chamber formed between the probe tip 204 and the fluidic sleeve 208. The fluid injected into the process passes out of the annular opening 210 of the fluidic sleeve 208. As discussed previously, one problem with the design of existing phacoemulsification probes is that the aspiration of emulsified materials occurs generally in the direction indicated by arrow 212 while the fluid injected into the process from the chamber between the fluidic sleeve 208 and the probe tip 204 occurs generally in the direction indicated by arrow 214. Thus, the aspirated materials and the fluids injected into the process are occurring in opposite directions working against each other.

Figure 3A:
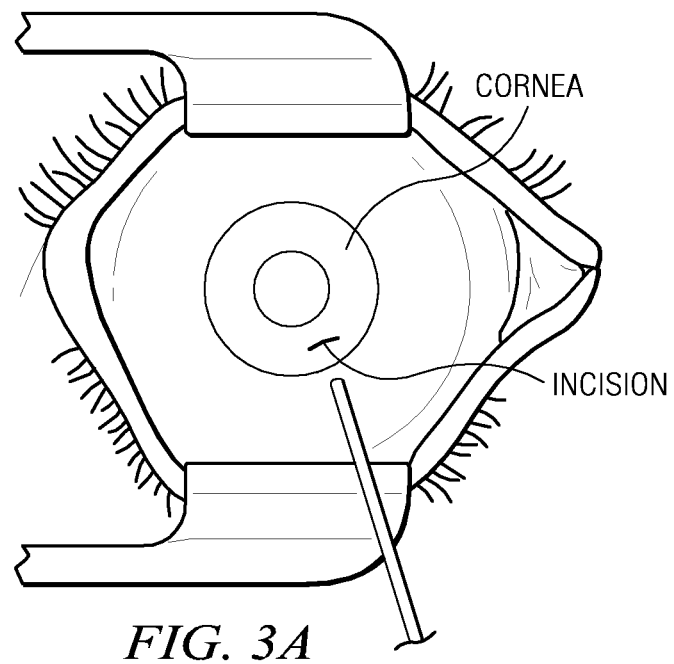
FIGS. 3*a*-3*e* illustrate the various steps involved in the use of a phacoemulsification probe with respect to cataract surgery.

Referring now to FIGS. 3a-3e, there are more fully illustrated the various processes involved within the phacoemulsification surgery procedure. Initially, as generally indicated at FIG. 3a, a micro incision of 1 mm-3 mm is made in the human eye at the junction of the clear cornea and the white of the eye (i.e., a clear corneal incision) to facilitate placement of the instrumentation for performing the phacoemulsification procedure. A side incision is also made. According to one technique these micro incisions are made either directly on the axis of the astigmatism of the patient's eye, or 90 degrees away from it, depending on the ease of access of surgery and the requirement for correction of astigmatism pre or post operatively.

Once the incisions have been made, a viscoelastic substance is injected into the eye to maintain intraocular pressure. The viscoelastic substance is injected within the anterior chamber 104 described previously with respect to FIG. 1. This procedure is analogous to performing a procedure within a water balloon while maintaining the pressure within that water balloon without releasing the fluid from the pressurized structure. Once the viscoelastic substance is injected within the anterior chamber 104 of the human eye, a circular opening is made within the anterior capsule 114 to create access to the lens 112. The removal of the anterior surface of the lens capsule is referred to as capsulorhexis.

Figure 3B:
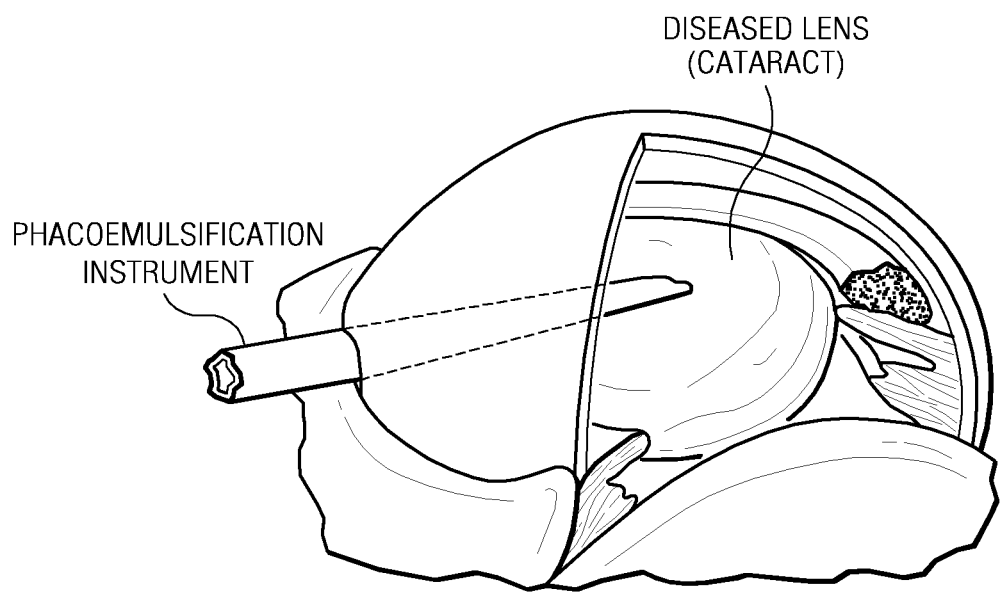
Figure 3C:
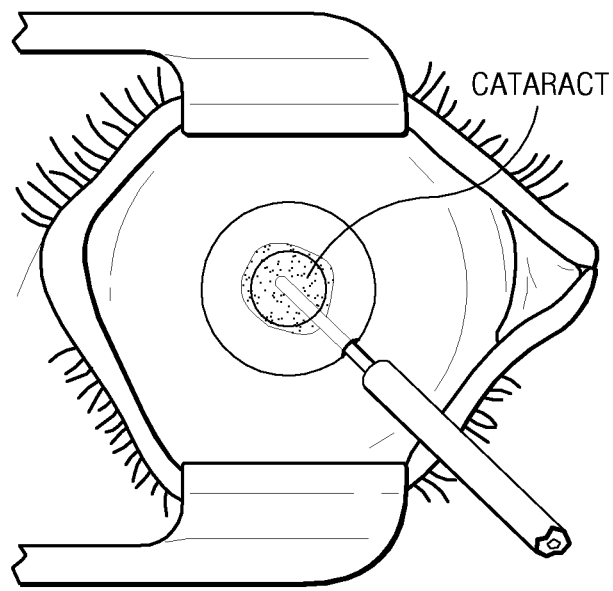

The phacoemulsification probe is inserted through the incision within the cornea as illustrated in FIG. 3b to enable access to the lens 112 via the hole made within the anterior capsule 114. Using ultrasonic emissions from the probe, the cataract within the lens 112 of the eye is broken up (emulsified) as illustrated generally in FIGS. 3b and 3c. The emulsified cataract material and lens is aspirated from the capsular sac using a combination of fluids injected within the capsular sac from the phacoemulsification probe and the aspiration functionalities of the probe.

This procedure can be analogized with the capsular sac being considered to be a common candy such as an M&M. The circular opening is made within the candy coating of the M&M on its anterior surface (i.e., capsulorhexis). The chocolate within the candy coating is then emulsified and aspirated from within the candy coating. This leaves a c-shaped bowl comprising the posterior surface of the M&M. In the present disclosure, the c-shaped bowl comprising a saran wrap-like biological tissue called the posterior capsule is allowed to remain within the eye to support a replacement lens inserted within the capsular sac as described hereinbelow.

Once the cataract and lens fragments have been aspirated from the capsular sac additional viscoelastic fluid may be injected into the empty capsular sac to expand it to facilitate placement of a folded intraocular lens (IOL). A foldable intraocular lens implant is made of silicon or acrylate and has the appropriate power of correction for the patient's vision. A folded IOL replaces the existing crystalline lens of the eye that has been removed due to the cataract. It normally comprises a small plastic lens with acrylate or silicone side struts, called haptics, to hold the lens in place within the capsular sac of the eye. The prescription of the IOL is established by the patient and the doctor in accordance with the needs of the patients such as is done for glasses or contact lenses.

Figure 3D:
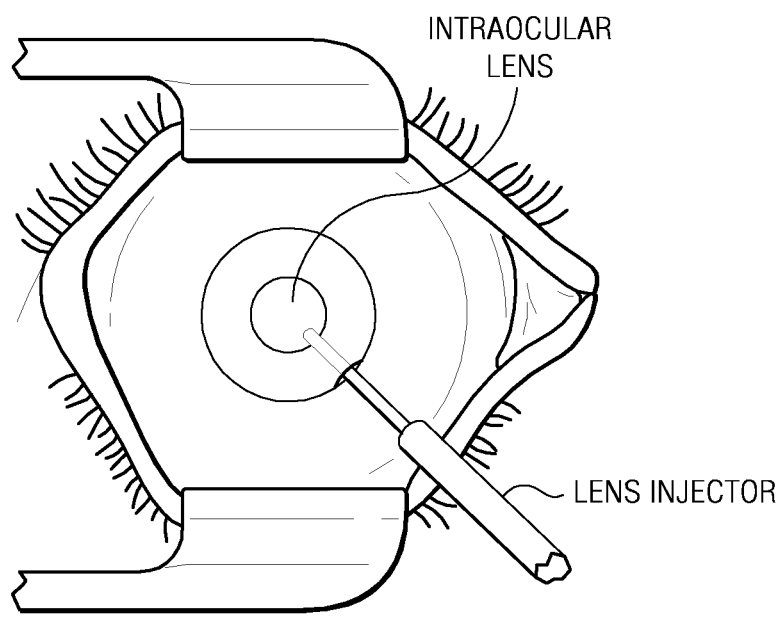
Figures 3E, 4A:
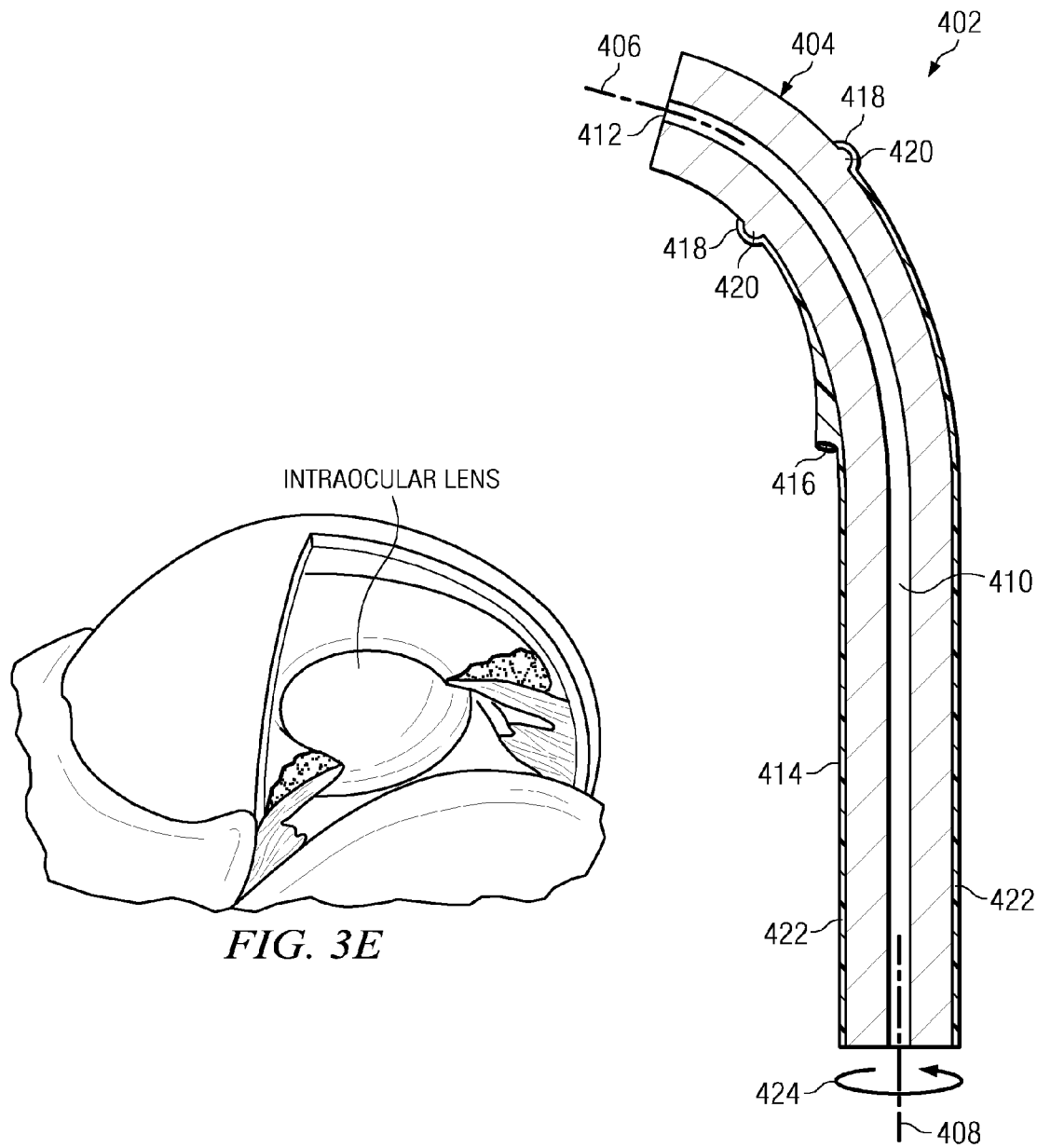
FIG. 4*a* provides a cross-sectional view of the phacoemulsification tip and associated sleeve of the present disclosure.

The IOL is injected within the capsular sac as illustrated in FIG. 3d using a lens injector through the incision that was previously used by the phacoemulsification probe. The use of a foldable IOL enables the lens to be rolled for insertion into the capsular sac through the very small incision made previously thus avoiding the need for stitches in the eye caused by a larger incision. After injection within the capsular sac using the lens injector as illustrated in FIG. 3d, the intraocular lens expands within the capsular sac as illustrated in FIG. 3e. The intraocular lens is supported by the posterior portion of the capsular sac which remains intact. The injected viscoelastic material may then be removed via aspiration and no sutures are required after the surgery due to the small size of the incisions that were made.

Referring now to FIG. 4a, there is illustrated the phacoemulsification probe and fluidic sleeve of the present disclosure. The phacoemulsification probe 402 rather than comprising a straight probe tip includes a curved probe tip 404. The end of the probe tip 404 is curved such that the axis 406 at the end of the tip is at an angle of approximately 20-45 degrees with respect to the main axis 408 of the probe tip 404. However, it should be realized that the angle between the curved portion of the probe tip 404 and the main axis 408 of the probe 402 could be set to any angle. The phacoemulsification probe tip 404 is constructed of titanium, stainless steel or other type of metallic material useful in surgical procedures. The opposite end of the probe tip 404 connects with a connector for connecting to the main probe body. The probe tip 404 also defines therein a passageway 410 enabling the aspiration of materials from the eye of a patient through an opening 412. The probe tip 404 is also connected to additional components within the probe body and probe machine enabling the probe tip 404 to vibrate at and emit ultrasonic frequencies. In addition to the ultrasonic vibrations, the tip 404 may be made to rotate along a circular axis 424 about the central axis 408 of the probe tip. The vibration of the probe tip 404 at the ultrasonic frequencies enables a surgeon to sculpt and emulsify cataracts or natural lenses while suctioning the aspirated particles into the opening 412 and the hollow passageway 410 running through the body of the tip 404.

Surrounding the body of the probe tip 404 is a fluidic sleeve 414. The fluidic sleeve 414 is made of silicon, plastic or metallic material and includes an aperture 416 enabling the expulsion of a fluid in an initial direction away from the opening 412 that is used for aspirating materials into the phacoemulsification probe 402. This enables fluid to be expelled in a non-competitive vector to the vector of suction. The end of the fluidic sleeve 414 closest to the opening 412 of the probe tip 404 is closed by having its edges 418 slide over a protrusion 420 within the body of the probe tip 404. The protrusion 420 is an annular protrusion completely surrounding the exterior surface of the probe tip 404. The protrusion 420 enables the open end 418 of the fluidic sleeve 414 to fit snugly over the probe tip 404 and seal the end of the fluidic sleeve such that any fluid injected into the sleeve will pass out the aperture 416. Fluid is provided to the aperture 416 through an annular area 422 that is defined between the inner wall of the fluidic sleeve 414 and the outer surface of the probe tip 404.

Figure 4B:
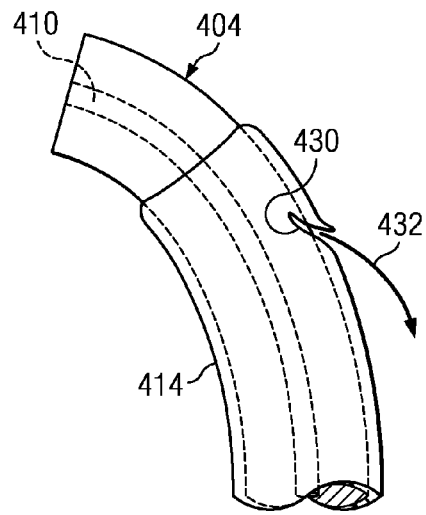
FIG. 4*b* illustrates an alternative embodiment of the fluidic sleeve.

Referring now also to FIG. 4b, there is illustrated an alternative embodiment wherein the fluidic sleeve 414 rather than having an aperture 416 on the inner radius of the probe tip includes an aperture 430 on the external radius of the probe tip. In this case, the vector of expulsion 432 would still be non-competitive with the vector of aspiration into the general 410 of the probe tip 404. Additionally, it is noted that the configuration of the aperture 430 illustrated in FIG. 4b is a shark gill configuration comprising a curved slit in the fluidic sleeve 410. Rather than using only a single slit for the aperture 430, multiple slits may be utilized in alternative configurations. It is noted that placement of the fluid aperture for the fluidic sleeve 410 on the external radius of the probe tip or the internal radius of the probe tip may be selected based upon a particular application of the probe tip. Thus, depending upon the application, the vector of expulsion 432 of the fluidic sleeve 414 may be configured in any number of directions that are non-competitive with the vector of aspiration of the probe tip in order to better provide different uses of the probe tip. Additionally, rather than the shark fin configuration illustrated in FIG. 4b or the small opening configuration illustrated in FIG. 4a any number of configurations may be utilized for the fluid aperture from the fluidic sleeve 414.

Figure 5:
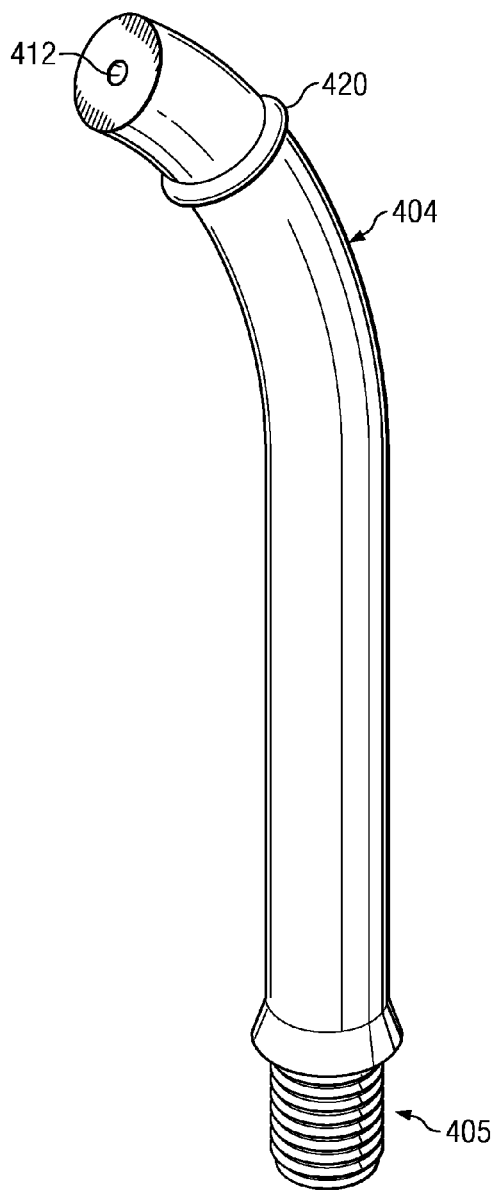
FIG. 5 illustrates the phacoemulsification probe tip of FIG. 4 with the sleeve removed.

Referring now to FIG. 5, there is illustrated a perspective view of the probe tip 404 having a first diameter. As described previously, the probe tip 404 is made of a metallic material and defines an opening 412 for aspirating materials removed from a patient's eye in the end of the probe 404. The annular protrusion 420 having a second diameter larger than the first diameter of the probe tip 404 is used for sealing the open end of the fluidic sleeve 414 as described hereinabove. The annular protrusion 420 surrounds the body of the probe tip 404 and is axially displaced from the end of the probe tip defining the opening 412 along an axis of the end of the probe tip defining the opening. A portion of the probe tip 404 extends from the end of the probe tip defining the opening 412 to the annular protrusion 420. Connector 405 allows connection of the probe tip 404 to the rest of the body of the phacoemulsification probe 402.

Figure 6:
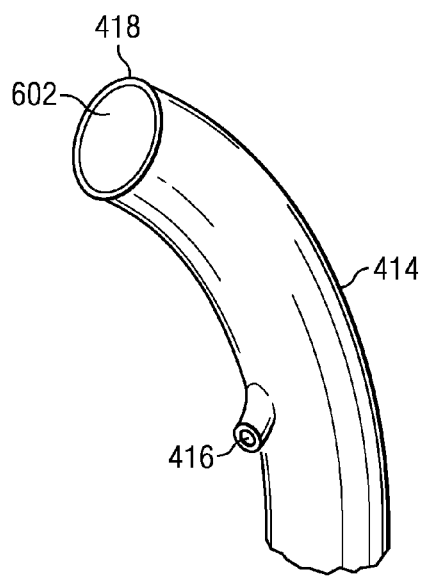
FIG. 6 illustrates the sleeve that is placed over the phacoemulsification probe tip.

Referring now also to FIG. 6, there is provided an illustration of the fluidic sleeve 414 which surrounds the probe tip 404. The top edge 418 of the fluidic sleeve 414 defines an opening through which the probe tip 404 is inserted. The opening 602 is sealed by the top edge 418 fitting snugly over the protrusion 420 on the phacoemulsification probe tip 404. The fluidic sleeve 414 is also curved at an angle similar to that of the phacoemulsification probe tip 404 such that a consistent sizing of the annular region 422 between the inner wall of the fluidic sleeve 414 and the external wall of the probe tip 404 is provided. Since the opening 602 of the fluidic sleeve 414 is sealed closed by the snug fit of edge 418 over the protrusion 420, all fluids which are expelled from the fluidic sleeve are expelled through the aperture 416. The configuration of the aperture 416 can be established to enable the fluids to be expelled in any desired direction, opposite that from the material which is being aspirated into the opening 412 of the probe tip 404.

Figure 7:
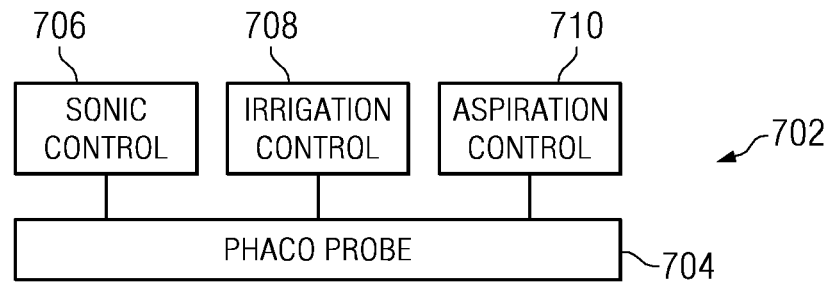
FIG. 7 is a functional block diagram of a phacoemulsification machine.

Referring now also to FIG. 7, there is illustrated a functional block diagram of a phacoemulsification machine 702 and an associated phacoemulsification probe 704. The phacoemulsification machine 702 includes sonic control components 706 for controlling the ultrasonic vibrations of the probe 704 for breaking up the cataract and lens structures, an irrigation control component 708 for controlling the flow of material through the chamber between the fluidic sleeve and the probe tip and aspiration control components 710 for controlling the aspiration of cataract and lens material from the capsular sac. The phacoemulsification machine 702 and probe 704 enables the integration into a single unit the irrigation, aspiration and ultrasound capabilities needed to break up and remove cataractous lenses from the eyes. An optical surgeon activates these capabilities in succession typically by depressing a foot pedal 712 associated with the phacoemulsification machine 702.

Initially, irrigation is provided by the irrigation controlled component 708 to the probe 704 typically by gravity feed from a bottle to flush the surgical site, maintain pressure in the anterior chamber of the eye to keep it from collapsing when aspiration is applied and to cool the probe tip during oscillations. Next, the aspiration control components 710 are activated to draw fluid and lens fragments toward and through the probe tip into a collection container. The aspiration components 710 employ different ophthalmic surgical systems such as a peristaltic pump, a venturi or diaphragm pump, etc. in order to perform the aspiration functions. The ultrasound control component 706 initiates the ultrasonic vibrations in order to emulsify the lens of a patient.

Maintaining control of the phacoemulsification probe 704 requires that the surgeon be able to achieve a balance between irrigation and the parameters of flow and vacuum. Flow describes the rate at which fluid and lens fragments travel toward and through the probe tip 404. The vacuum describes the suction force that holds material to the probe tip. During surgery, aspiration draws the lens and lens fragments toward the probe tip and the vacuum holds the lens or fragments at the tip while the ultrasonic waves push them away. The effects of both cavitation and mechanical impact cause the lens material to break apart. When small enough, the fragments are aspirated through the probe tip at a rate determined by the aspiration rate. Too high a flow rate will cause fragments to move too fast, creating turbulence within the eye. Too high a vacuum can cause a surge after an occluded lens piece is quickly emulsified.

The phacoemulsification machine 702 allows surgeons to control the aspiration parameters using either a fixed or linear mode of operation. In fixed modes, the unit provides aspiration at a set level as established by the aspiration control component 710 when the surgeon depresses the foot pedal. In linear mode, the surgeon's increasing depth of foot pedal depression controls one of the aspiration parameters. Operating the unit at a fixed mode is relatively straight forward. However, achieving the desired clinical performance also requires an understanding of the unit's linear mode of operation.

Figure 8:
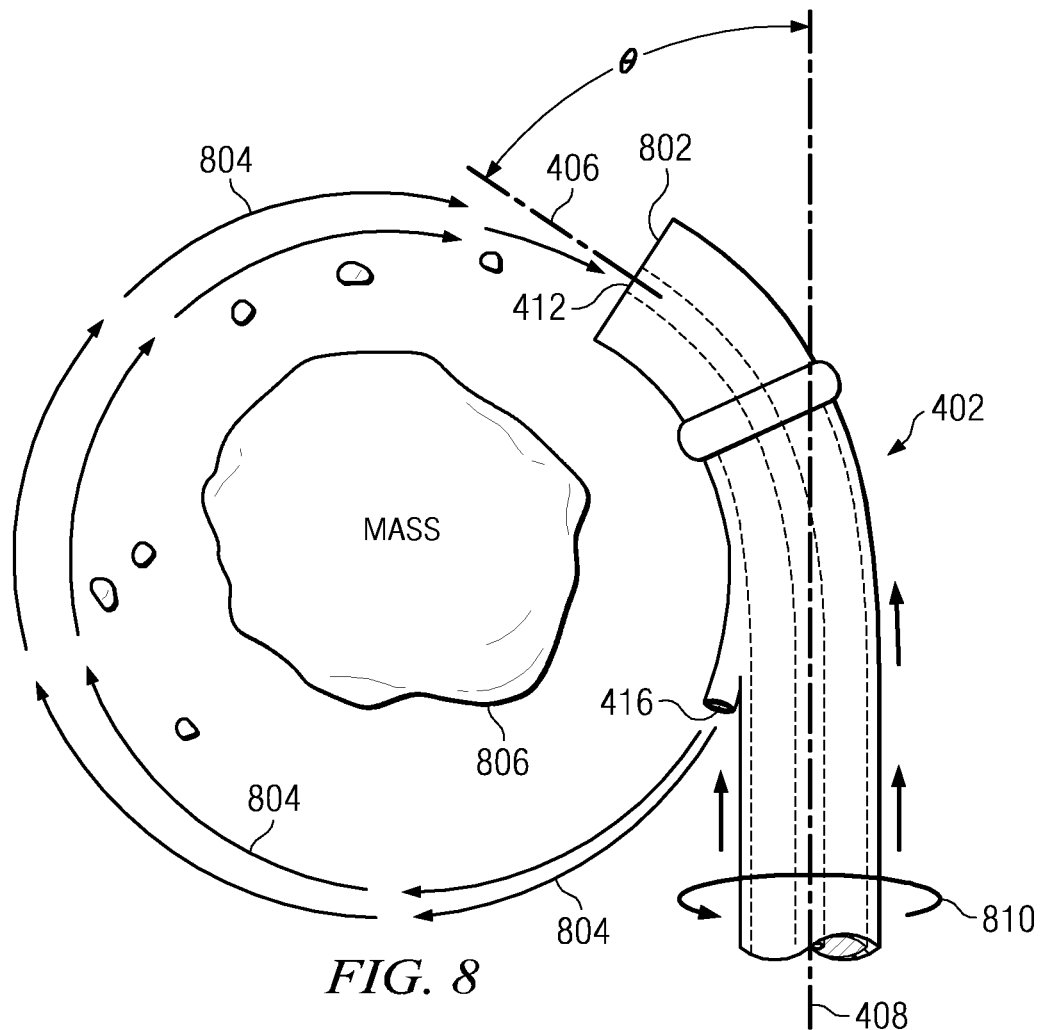
FIG. 8 illustrates the various force vectors which may be utilized within utilizing the phacoemulsification probe tip to remove a mass such as a cataract within an eye.

Referring now to FIG. 8, there are illustrated the various forces used by the phacoemulsification probe 402 to remove lens material from the capsular sac of an eye. As described previously, the curvature of the probe tip may be such that the angle between the axis 406 of the opening for aspirating material from an eye and the main axis 408 of the probe 402 can be an angle θ anywhere between 20 and 45 degrees. However, angles of other values may also be utilized. The curved shape of the probe 402 and the aperture 416 providing the fluid infusion to the capsular sac that does not oppose the direction of aspiration provides several advantages over existing phacoemulsification probe configurations. The curved tip provides a configuration wherein the coaxial ultrasound generation along axis 408 provides non-coaxial tip movement at the probe tip 802. Additionally, the curvature of the probe tip enables, with a slight rotation of the surgeon's hand, a three-dimensional movement of the tip 802 within the eye. This facilitates the emulsification procedure and enables the surgeon to generate tip movement in a circumlinear fashion within the capsular bag. This allows the direction of aspiration into opening 412 to be centrifugal to the human lens substance. The curvature also enables the ultrasonic energy of emulsification to be directed in a two dimensional fashion via the curved tip design along the main axis 408 and along the axis 406 of the curved end and allows the tip to move three dimensionally facilitated by the surgeon's movement and control of the rotational aspects of the emulsification probe 402. Thus, the probe tip 802 may be placed within the circumference of the cataract and allows the aspiration to function in a centrifugal fashion, removing the lens material in a plane parallel to the plane of the iris and parallel to the plane of the human lens equator. This is different from the to and fro motion of straight tip phacoemulsification probe configurations described previously in prior art designs.

In addition to the sonic vibrations, the probe tip may be made to rotate along a circular axis 810, as illustrated in FIG. 8, to create additional ultrasonic vibrations for breaking up cataract or lens materials. Using the described configuration, the probe tip will have three degrees of motion. The axis of ultrasonic vibration in the motion of the tip may first move along the main axis 408 parallel to the long axis of the probe. The tip may also vibrate along a second axis 406 obliquely displaced from the long axis of the tip by virtue of the curved and beveled tip of the probe. Finally, the tip may have included therewith coaxial rotation about an axis 810 either generated by the surgeon or by coaxial rotation of the tip generated by additional ultrasonic components.

Additionally, the fluidic sleeve design having the opening 416 to provide for fluid infusion that does not compete with the direction of aspiration of the probe tip provides a cyclonic movement of fluid within the eye as opposed to fluidic infusion directly in competition with the vector of aspiration. As can be seen in FIG. 8, fluid is ejected from opening 416 in a direction illustrated generally by arrows 804. Similar motion can be provided by an aperture on the external radius of the sleeve. The combination of the shape of the capsular sac, the direction of the fluid from the opening 416 and the aspiration into opening 412 of the probe tip 404 contributes to the cyclonic motion of the fluid within the eye around any mass 806 that is being emulsified by the ultrasonics of the probe tip 404. As particles of the mass 806 are broken down into a small enough size by ultrasonic vibrations of the probe tip 404 by bimanually dismantling the nucleus, the cyclonic motion of the fluid in the eye rotates the emulsified particles to the opening 412 of the probe tip enabling them to be aspirated out of the capsular bag. Thus, the cyclonic movement of the fluid within the eye directs the lens materials toward the opening 412 of the probe tip rather than creating force vectors that would direct emulsified components away from the aspiration of the probe tip.

Figure 9A:
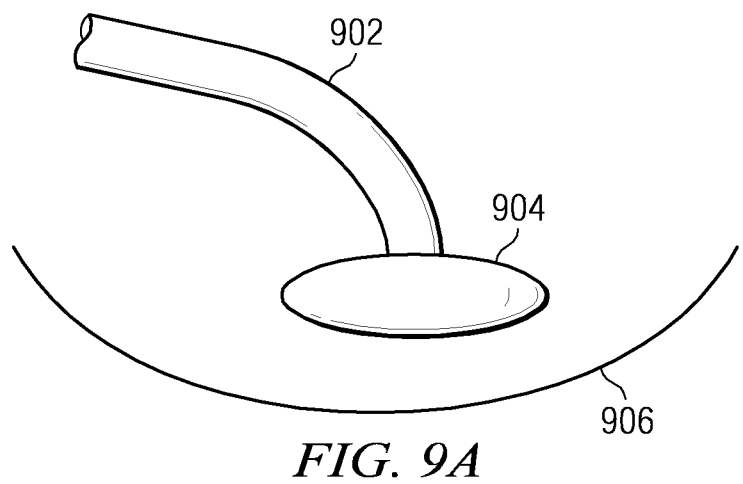
FIGS. 9*a* and 9*b* illustrate a further use of the probe.
Figure 9B:
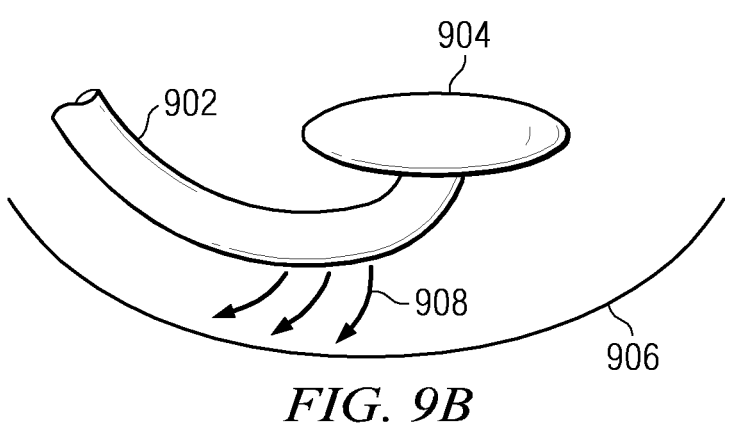

The improved configuration of the probe provides a number of advantages over the prior art. The described configuration is specifically adaptable to hard nuclei whereby a more anterior emulsification of a hard lens causes turbulent endotheliopathy and damage to the insides of the cornea. The more linear to and fro motion of a straight or beveled tip probe places more stress on the support structures of the human lens (zonules). With the probe tip described herein, the forces are more indirectly directed against the hard nuclei. The stresses upon the zonules are minimized when treating large hard nuclei using a process wherein the hard nuclei may be grasped by the tip of the probe 902 as shown generally in FIG. 9a. Once the hard nuclei has been grasped, the probe tip may be rotated such that the hard nuclei and associated lens are moved away from the anterior portion of the capsular sac 906. When the hard nuclei 904 is moved away form the anterior portion capsular sac 906 as illustrated generally in FIG. 9b, the fluid vectors 908 from the aperture of the fluidic sleeve 910 of the probe tip 902 assist in keeping the capsular sac 906 open and away from the hard nuclei 904. The surgeon my then dissect the hard nuclei 906 into as many pieces as necessary in order to assist in it's aspiration through the probe tip.

This method is also efficient in removing softer, more gelatinous lens material from younger patients, or patients with less nuclear hardening for the purposes of early cataract removal, refractive lensectomy or presbyopic lens exchange. A configuration of the described lens probe results in fewer complications, such as endothelial cell trauma, retinal detachment, corneal edema, post-operative inflammation or wound treatment while facilitating better immediate post-operative visual acuity and function.

The angulation of the tip in a curved fashion from the main body thereof prevents coring of and plugging of lens material within the opening 412 by cataract or refractive or presbyopic lens substance. This prevents stopping or plugging during aspiration and facilitates improvement of coring problems caused during phacoemulsification procedures. The above-described configuration includes a number of improvements over existing designs with respect to the infusion vectors and aspiration and emulsification vectors that are competitive in existing configurations. There have not previously been designed or made available a tip and sleeve that utilizes the anatomy of a human lens as a guide, the generation of ultrasonic movements intentionally oblique to the coaxial vector of ultrasonic generation, the surgeon's control of the third rotational function of tip movement and to intentionally provide aspiration and infusion fluidics in opposite directions designed specifically to respect the lens anatomy and to facilitate aspiration by the thus created fluidics instead of to unknowingly compete with it. This combination generates a cyclonic fluidic rotation of the lens material and allows the lens material to move toward the aspiration tip within the capsular bag thus facilitating emulsification and aspiration removal of the lens material.

It will be appreciated by those skilled in the art having the benefit of this disclosure that this probe tip and infusion sleeve for use with ophthalmological surgery provides improvements over existing designs. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A phacoemulsification probe, comprising:
a first portion for interconnecting the probe with a phacoemulsification machine; and
a probe tip having a first diameter with a central axis running therethrough having a first end connected with the first portion and a second end with a second axis running therethrough, wherein the second axis is at a predetermined angle to the central axis, wherein the probe tip further includes a body defining a channel therein for aspirating material therethrough from a surgical region, the body including a straight portion connected to the first end and a curved portion connecting the straight portion to the second, the probe tip further including an annular protrusion having a second diameter larger than the first diameter, the annular protrusion surrounding the body and axially displaced from the second end along the second axis such that a portion of the probe tip extends from the second end to the annular protrusion.

2. The phacoemulsification probe of claim 1 further including a fluid sleeve which surrounds at least a portion of the probe tip and defines a channel between the fluid sleeve and the probe tip for injecting a fluid into the surgical region.

3. The phacoemulsification probe of claim 2, wherein the fluid sleeve further defines an aperture through which the fluid is injected into the surgical region, the aperture directing the fluid along a first vector that is not substantially competitive to a second vector of aspiration into the channel of the probe tip.

4. The phacoemulsification probe of claim 2, wherein the fluid sleeve further defines an aperture through which the fluid is injected in the surgical region, the aperture directing the fluid along a first vector that is substantially a same direction as a second vector of aspiration into the channel of the probe tip.

5. The phacoemulsification probe of claim 4, wherein a combination of the aspiration from the surgical region into the channel of the probe tip and injection of fluid from the aperture into the surgical region creates a vortex within the surgical region from the aperture to the channel.

6. The phacoemulsification probe of claim 1, wherein the probe tip is configured to vibrate at ultrasonic frequencies.

7. The phacoemulsification probe of claim 1, wherein the probe tip is configured to circularly rotate about an axis running through the first end of the probe tip.

8. A phacoemulsification probe, comprising:
a first portion for interconnecting the probe with a phacoemulsification machine;
a probe tip having a first diameter with a central axis running therethrough having a first end connected with the first portion and a second distal end with a second axis running therethrough, wherein the second axis is at a predetermined angle to the central axis, wherein the probe tip further includes a body defining a channel therein for aspirating material therethrough from a surgical region along a first vector, the body including a straight portion connected to the first end and a curved portion connecting the straight portion to the second distal end, the probe tip further including an annular protrusion having a second diameter larger than the first diameter, the annular protrusion surrounding the body and axially displaced from the second distal end along the second axis such that a portion of the probe tip extends from the second end to the annular protrusion; and
a fluid sleeve which surrounds at least a portion of the body and defines a channel between the fluid sleeve and the body for injecting a fluid into the surgical region along a second vector, an end of the fluid sleeve securely fitting over the annular protrusion to substantially seal the end of the fluid sleeve, wherein the second vector is not substantially competitive with the first vector of aspiration of the probe tip.

9. The phacoemulsification probe of claim 8, wherein an aperture directs the fluid along the second vector that is substantially a same direction as the first vector of aspiration into the channel of the probe tip.

10. The phacoemulsification probe of claim 8, wherein a combination of the aspiration from the surgical region into the channel of the probe tip and injection of fluid from an aperture into the surgical region creates a vortex within the surgical region from the aperture to the channel.

11. The phacoemulsification probe of claim 8, wherein the probe tip is configured to vibrate at ultrasonic frequencies.

12. The phacoemulsification probe of claim 8, wherein the probe tip circularly rotates about an axis running through the first end of the probe tip.

13. A phacoemulsification probe, comprising:
a first portion for interconnecting the probe with a phacoemulsification machine;
a probe tip having a first diameter with a central axis running therethrough having a first end connected with the first portion and a second end with a second axis running therethrough, wherein the second axis is at a predetermined angle, wherein the probe tip further includes a body defining a channel therein for aspirating material therethrough from a surgical region along a first vector, the body including a straight portion connected to the first end and a curved portion connecting the straight portion to the second end, the probe tip further including an annular protrusion having a second diameter larger than the first diameter, the annular protrusion surrounding the body and axially displaced from the second end along the second axis such that a portion of the probe tip extends from the second end to the annular protrusion; and
a fluid sleeve which surrounds at least a portion of the probe tip and defines a channel between the fluid sleeve and the probe tip for injecting a fluid into the surgical region along a second vector, wherein an aperture directs the fluid along the second vector that is substantially a same direction as the first vector of aspiration into the channel of the probe tip, further wherein a combination of the aspiration from the surgical region into the channel of the probe tip along the first vector and injection of fluid from the aperture into the surgical region along the second vector creates a circular vortex within the surgical region from the aperture to the channel.

14. The phacoemulsification probe of claim 13, wherein the probe tip is configured to vibrate at ultrasonic frequencies.

15. The phacoemulsification probe of claim 13, wherein the probe tip circularly rotates about an axis running through the first end of the probe tip.

* * * * *